United States Patent [19]
Nicoll et al.

[11] Patent Number: 5,215,749
[45] Date of Patent: * Jun. 1, 1993

[54] COSMETIC COMPOSITION

[75] Inventors: Gregg A. Nicoll, Dumont, N.J.; Ian R. Scott, Wellingborough, England

[73] Assignee: Chesebrough-Pond's USA Co., Division of Conopco, Inc., Greenwich, Conn.

[*] Notice: The portion of the term of this patent subsequent to Feb. 23, 2010 has been disclaimed.

[21] Appl. No.: 698,433

[22] Filed: May 10, 1991

[30] Foreign Application Priority Data

May 10, 1990 [GB] United Kingdom ............... 9010527

[51] Int. Cl.$^5$ ............................................. A61K 7/42
[52] U.S. Cl. ..................................... 424/401; 424/49
[58] Field of Search ............................ 424/59, 63, 69

[56] References Cited
U.S. PATENT DOCUMENTS 4,119,712 10/1978 Goldner et al. ................ 424/69 X
5,008,101 4/1991 Klimisch et al. ..................... 424/59

FOREIGN PATENT DOCUMENTS 2533497 7/1975 Fed. Rep. of Germany .
3824999 7/1987 Fed. Rep. of Germany .
2184356 12/1986 United Kingdom .
2206282 6/1988 United Kingdom .
2211736 7/1989 United Kingdom .
2217987 11/1989 United Kingdom .

OTHER PUBLICATIONS

European Search Report.
British Patent Office Search Report.

Primary Examiner—Thurman K. Page
Attorney, Agent, or Firm—Milton L. Honig

[57] ABSTRACT

A composition for tonical application to human skin to provide protection from excessive exposure to ultraviolet rays, comprises:
a. an effective amount of ultrafine titanium dioxide as an inorganic sunscreen;
b. an effective amount of octyl methoxycinnamate as an organic sunscreen; and
c. a cosmetically acceptable vehicle for the sunscreens;
the weight concentration of the titanium dioxide and octyl methoxycinnamate being within the region designated A in the accompanying drawing.

9 Claims, 1 Drawing Sheet

COSMETIC COMPOSITION

FIELD OF THE INVENTION

The invention relates to compositions for topical application to human skin to provide enhanced protection from the damaging effects of sunlight.

BACKGROUND AND PRIOR ART

The damaging effects of sunlight on human skin have been observed since time immemorial and many remedies have been proposed to protect the skin from this damage.

In general terms, harmful ultra-violet (UV) rays, particularly those originating from sunlight, which penetrate the upper atmosphere and reach the earth's surface, can be classified into:

i. the energy-rich UV-B rays (290–320 nm wavelength) which possess an intense physiopathological activity on the skin; these are absorbed just above the dermis and they are responsible for erythema and skin pigmentation, and ii. UV-A rays (320–400 nm wavelength) which penetrate deeper into the skin (to the dermis and beyond). Their energy is much lower and the photobiological effects they cause are much more long term in nature, for example, they accelerate skin ageing.

Certain organic substances (sunscreens) whose molecules absorb the harmful ultra-violet rays have been proposed for use in mitigating the deleterious effects of ultra-violet radiation.

Some of these substances absorb more effectively in UV-A range thereby providing filtering of UV radiation in this range, while others are more effective in the UV-B range.

A common problem exists, however, whatever the choice of organic sunscreen, for protection from whichever wavelength of ultra-violet radiation, and this is that physiological damage to the body can occur, following topical application of these sunscreens in quantities necessary to provide effective filtering of harmful ultra-violet radiation. Even those organic sunscreens that are believed to be safe to use in this way, necessarily have safety limits imposed, based on the quantity applied to the skin, which can result in only moderate to poor protection from harmful ultra-violet radiation.

Certain inorganic substances have also been proposed for use as sunscreens which physically block exposure of the skin to ultra-violet rays. Notable of these is titanium dioxide having a very small particle size. This grade of titanium dioxide, designated ultrafine $TiO_2$, affords a good degree of sun blocking potential without the unacceptable skin whitening experienced with the normal pigmentary grade (particle size >300nm). For example, in DE-A-3824999 (The Boots Company PLC), it is proposed to use oil-dispersible titanium dioxide with a mean primary particle size of <100nm in a water-in-oil emulsion as a sunscreen preparation. This reference also suggests that organic sunscreen agents, such as p-aminobenzoic acid and esters thereof, methoxycinnamate, benzophenone, dibenzoylmethanes or salicylates can also be included to improve protection.

In spite of this, and other prior proposals, there still exists a need for a highly efficient and thoroughly safe sun protection composition which has a wide spectrum of protection (i.e. both UV-A and UV-B) in the UV region.

SUMMARY OF THE INVENTION

Applicants have now discovered that by the use of ultrafine titanium dioxide together with a specific organic sunscreen, whose concentration is lower than usual, in a composition adapted for use topically on the skin, synergistically enhanced protection from ultraviolet rays can be attained.

DEFINITION OF THE INVENTION

Accordingly, the invention provides a composition for topical application to human skin to provide protection from excessive exposure to ultra-violet rays, which comprises:

a. an effective amount of ultrafine titanium dioxide;
b. an effective amount of octyl methoxycinnamate; and
c. a cosmetically acceptable vehicle;

the weight concentration of the titanium dioxide and octyl methoxycinnamate being within the region designated A in the accompanying drawing.

DISCLOSURE OF THE INVENTION

The invention is concerned with a composition suitable for topical application to human skin to provide protection from excessive exposure to ultra-violet rays over a large range of wavelengths, notably covering both the UV-A and UV-B ranges. The composition of the invention comprises a special mixture of an inorganic sunscreen, namely ultrafine titanium dioxide and an organic sunscreen namely octyl methoxycinnamate, which are both conveniently dispersed or distributed in a cosmetically acceptable vehicle. Depending upon the nature of the composition, other sunscreens, skin benefit materials and/or cosmetic adjuncts can optionally be present in the composition.

The titanium dioxide

The composition according to the invention comprises ultrafine titanium dioxide.

Ultrafine titanium dioxide is available as a water-dispersible form and as an oil-dispersible form: either or both forms of titanium dioxide can be employed in the composition according to the invention.

By "ultrafine titanium dioxide" is meant titanium dioxide having an average particle size of less than 100 nm, preferably from 10 to 40nm and most preferably from 15 to 25 nm.

Water-dispersible titanium dioxide is ultrafine titanium dioxide, the particles of which are uncoated or which are coated with a material to impart a hydrophilic surface property to the particles. Examples of such materials include aluminium oxide and aluminium silicate.

Oil-dispersible titanium dioxide, is ultrafine titanium dioxide, the particles of which exhibit a hydrophobic surface property, and which for this purpose can be coated with metal soaps, such as aluminium stearate, aluminium laurate or zinc stearate, or with organosilicone compounds.

The organic sunscreen

The composition according to the invention also comprises as the organic sunscreen octyl methoxycinnamate, an example of which is Parsol MCX available from Bernel Chemical Co.

The concentration of the titanium dioxide and the octyl methoxycinnamate

It is well known to those skilled in the art that different sunscreens can be combined in a formulation to achieve high sun protection factors. Different sunscreens have different absorption coefficients however and as a consequence equal weights of sunscreens do not necessarily give equal sun protection.

Given this caveat, it would be expected that combinations of sunscreens would have additive effects such that where:

X = the concentration of the first sunscreen required, on its own, to produce an SPF of S.
Y = the concentration of the second sunscreen required, on its own, to produce an SPF of S.

both sunscreens being formulated in otherwise identical formulations, then the same formulation containing concentrations of:

| |
|---|
| Xn parts of the first sunscreen, and, Y(1-n) parts of the second sunscreen, where n is between 0 and 1 would also give an SPF of S $\quad$ Expression 1 |

The Accompanying Drawing

An extensive series of experiments has been carried out to test this theoretical prediction and it has been established that it does, in fact, hold for most mixtures of octyl methoxycinnamate and ultrafine titanium dioxide, such that the difference between the theoretical erythemally effective UV light transmission (which is equal to 100/SPF) and the actual erythemally effect UV light transmission is less than 1%. However, certain particular mixtures of these sunscreens produce an actual transmission significantly less than that predicted by theory and thereby produce statistically significantly better UV protection than expected.

BRIEF DESCRIPTION OF THE DRAWING

These preferred compositions are defined by the area designated A in the accompanying drawing, FIG. 1, in which the ordinate represents % by weight octyl methoxycinnamate in the composition, and the abscissa represents % by weight ultrafine titanium dioxide in the composition. Particularly preferred compositions are defined by area B, especially preferred compositions by area C, more preferred compositions by area D and most preferred compositions by area E.

By inspection, it can be deduced that the approximate weight concentrations of ultrafine titanium dioxide and octyl methoxycinnamate for each of the designated areas are as follows, bearing in mind that the combined amounts of the titanium dioxide and octyl methoxycinnamate should fall within the appropriate area designated in the drawing.

Figure 1:
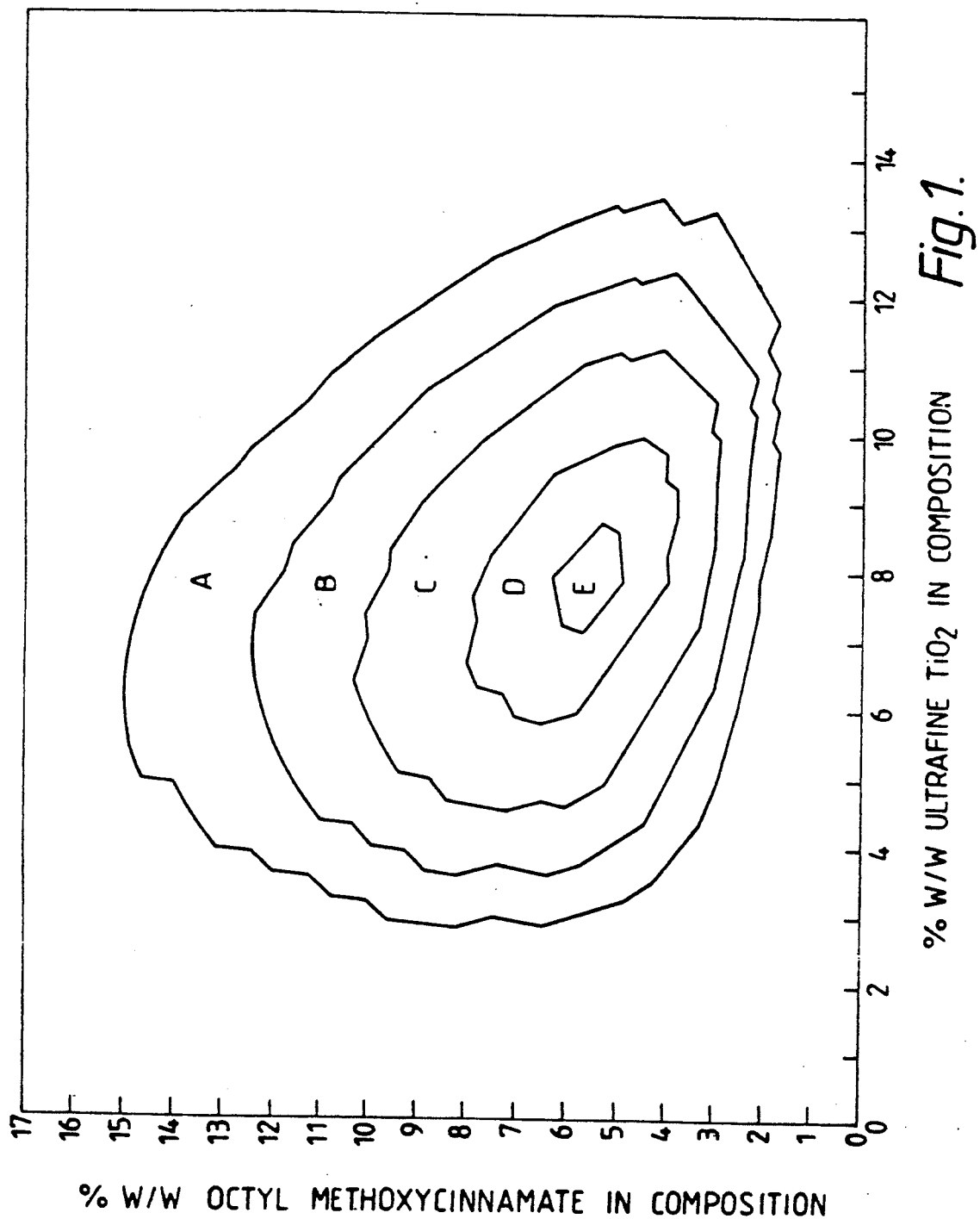

| Area Designated | Approximate % concentration | |
|---|---|---|
| | ultrafine TiO$_2$ | octyl methoxycinnamate |
| A | 3 to 13 | 2 to 15 |
| B | 4 to 12 | 2 to 12 |
| C | 5 to 11 | 3 to 10 |
| D | 6 to 10 | 4 to 8 |
| E | 7 to 9 | 5 to 6 |

It is also apparent that when the composition contains less than 2% by weight of octyl methoxycinnamate, the amount of protection afforded by the composition following topical application to human skin is very low, whereas when the amount of this ingredient exceeds 10% by weight of the composition then, although the degree of protection against ultra-violet rays afforded by the composition following topical application to skin is substantial, the amount of this ingredient in the composition is sufficiently high to give some cause for anxiety as to the safety in use of this composition when applied topically to human skin.

The Cosmetically Acceptable Vehicle

The composition according to the invention also comprises a cosmetically acceptable vehicle to act as a dilutant, dispersant or carrier for other materials present in the composition, so as to facilitate their distribution when the composition is applied to the skin and/or hair.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, jojoba oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants, such as propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the emulsion, and can, in the absence of other cosmetic adjuncts, form the balance of the emulsion.

OPTIONAL SKIN BENEFIT MATERIALS AND COSMETIC ADJUNCTS

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

Oil or oily material

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

Emulsifier

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 1 in which the chemical name of the emulsifiers is given together with an example of a trade name as commercially available, and the average HLB value.

TABLE 1

| Chemical Name of Emulsifier | Trade Name | HLB Value |
| --- | --- | --- |
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |

TABLE 1-continued

| Chemical Name of Emulsifier | Trade Name | HLB Value |
| --- | --- | --- |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene 20 sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

Water

The composition of the invention can also comprise water, usually up to 80%, preferably from 5 to 80% by volume.

Silicone Surfactant

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

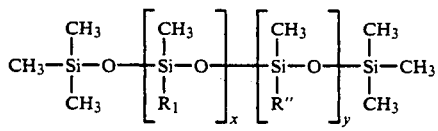

where
the groups R' and R" are each chosen from —H, $C_{1-18}$ alkyl and $$-[CH_2CH_2O]_a[CH_2CHO]_bH$$
$$\phantom{-[CH_2CH_2O]_a[CH_2C}|$$
$$\phantom{-[CH_2CH_2O]_a[CH_2CH}CH_3$$

a has a value of from 9 to 115,
b has a value of from 0 to 50,
x has a value of from 133 to 673,
y has a value of from 25 to 0.25.

Preferably, the dimethyl polysiloxane polymer is one in which:
a has a value of from 10 to 114
b has a value of from 0 to 49
x has a value of from 388 to 402
y has a value of from 15 to 0.75
one of groups R' and R" being lauryl, and the other having a molecular weight of from 1000 to 5000.

A particularly preferred dimethyl polysiloxane polymer is one in which:
a has the value 14
b has the value 13
x has the value 249
y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Further organic sunscreens

The emulsion of the invention optionally can comprise one or more organic sunscreens, in addition to octyl methoxycinnamate, further to enhance the benefit of the emulsion in providing protection from the harmful effects of excessive exposure to sunlight.

As has already been stated, some organic sunscreens can be harmful to health if applied topically to the skin at a concentration sufficient to screen out effectively radiation from either the UV-A range or the UV-B range. The presence however, of ultrafine titanium dioxide, which can provide a broad spectrum of protection, enables a lower than usual amount of organic sunscreen materials to be used to "top-up" the overall Sun Protection Factor of the emulsion to an exceptionally high level, without the risk of causing the type of skin damage or other health problems that can be associated with the use of higher levels of organic sunscreen materials alone.

In view of this, a relatively small amount of a second organic sunscreen optionally can be incorporated into the emulsion of the invention.

Examples of suitable further organic sunscreens, in addition to octyl methoxycinnamate, when required, include those set out in Table 2 below, and mixtures thereof.

TABLE 2

| CTFA Name | Trade Name | Supplier |
|---|---|---|
| Benzophenone-3 | UVINUL M-40 | BASF Chemical Co. |
| Benzophenone-4 | UVINUL MS-40 | BASF Chemical Co. |
| Benzophenone-8 | SPECRA-SORB UV-24 | American Cyanamide |
| DEA Methoxcinnamate | BERNEL HYDRO | Bernel Chemical |
| Ethyl dihydroxy-propyl-PABA | AMERSCREEN P | Amerchol Corp. |
| Glyceryl PABA | NIPA G.M.P.A. | Nipa Labs. |
| Homosalate | KEMESTER HMS | Hunko Chemical |
| Methyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl salicylate | SUNAROME WMO | Felton Worldwide |
| PABA | PABA | National Starch |
| 2-Phenyl-benzimidazole--5-sulphonic acid | EUSOLEX 232 | EM Industries |
| TEA salicylate | SUNAROME W | Felton Worldwide |
| 3-(4-methylbenzy-lidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy di-benzoyl methane | PARSOL 1789 | Givaudan Corp. |
| Etocrylene | UVINUL N-35 | BASF Chemical Co. |

The composition of the invention can accordingly comprise from 0.1 to 10%, preferably from 1 to 5% by weight of an organic sunscreen material.

Other Inorganic Sunscreens

The emulsion of the invention optionally can comprise an inorganic sunscreen in addition to ultrafine titanium dioxide as herein defined.

Examples of other inorganic sunscreens include:
zinc oxide, having an average particle size of from 1 to 300nm,
iron oxide, having an average particle size of from 1 to 300nm,
silica, such as fumed silica, having an average particle size of from 1 to 100 nm.

It should be noted that silica, when used as an ingredient in the emulsion according to the invention can provide protection from infra-red radiation.

Other Cosmetic Adjuncts

Examples of conventional adjuncts which can optionally be employed include preservatives, such as para-hydroxy benzoate esters; antioxidants, such butyl hydroxy toluene; humectants, such as glycerol, sorbitol, 2-pyrrolidone-5-carboxylate, dibutylphthalate, gelatin, polyethylene glycol, such as PEG 200-600; buffers, such as lactic acid together with a base such as triethanolamine or sodium hydroxide; waxes, such as beeswax, ozokerite wax, paraffin wax: plant extracts, such as Aloe vera, cornflower, witch hazel, elderflower, cucumber; thickeners; activity enhancers; colourants; and perfumes. Cosmetic adjuncts can form the balance of the composition.

Use of the Composition

The composition according to the invention is intended primarily as a sun care product for topical application to human skin to protect exposed skin from the harmful effects of excessive exposure to sunlight.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

PRODUCT FORM AND PACKAGING

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above.

The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

Method for Determining Concentrations of Octyl Methoxycinnamate and Ultrafine Titanium Dioxide To determine the optimum concentration of the two sunscreens it is necessary to have an accurate and convenient method to measure the Sun Protection Factor (SPF) of a relatively large number of formulations. Any suitable method can be used, including the DIN or FDA approved in vivo methods but the in vitro method described below is particularly accurate and convenient. All formulations used were based on a simple commercial O/W emulsion sunscreen base composition.

The method for the in vitro SPF determination of the composition of the invention involves the spectrophotometric scanning of stratum corneum between 400 nm and 290 nm utilising a Perkin Elmer Lamba 17 spectrophotometer equipped with a diffuse transmission detection system.

Transpore ® tape is used in place of human skin and the following procedure is followed.

i. A piece of the tape is applied to the outer surface of a 0.5 cm quartz cuvette.
ii. The quartz cuvette carrying the piece of tape is placed in the light path of the spectrophotometer which for this purpose is fitted with a fluorescence cut-off filter. This filter eliminates the autofluorescence of the tape and filters out all transmissions above 400 nm.
iii. The tape is scanned from 290 to 400nm and the spectrum obtained is saved as the control.
iv. The cuvette with tape is removed from the spectrophotometer and the test material (i.e. sunscreen) is applied to the tape at the rate of 1.5 $\mu$l/cm$^2$, in accordance with German DIN protocol, and rubbed uniformly across the entire surface of the tape using the finger fitted with a finger stall.
v. The applied sunscreen material is allowed to stand for 5 minutes at room temperature (20° C.) to enable it to dry, and then the sample is rescanned in the spectrophotometer as before from 290 to 400 nm. This spectrum is saved as the test spectrum. No spectral absorbance changes were observed with drying times between 2 and 15 minutes; the 5 minute drying time was therefore adopted as standard.
vi. The control spectrum is subtracted from the test spectrum to provide the spectral absorbance of the test sample of sunscreen material and this absorbence is converted to transmission.
vii. The in vitro Sun Protection Factor (SPF) is finally calculated from the transmission measurements as described by Diffey et al, in a paper entitled: "A new substrate to measure sunscreen protection factors throughout the ultra-violet spectrum" in J. Soc. Cosmet. Chem. 40, 127–133 (May/June 1989); see especially page 130.

This process provides accurate SPF values for a variety of formulations. From the data for SPF of formulations containing simple sunscreens, values of X and Y in Expression 1, for S values of 1 to 50, are obtained using interpolation or extrapolation where necessary. Actual SPF values are then obtained for mixtures of the two sunscreens with n - 0, 0.02, 0.04 . . . 1.00 in Expression 1. Again, precise data points are obtained by computer-assisted interpolation and extrapolation of actual data points with the assumption that, within the range of the extrapolation or interpolation, Beer's law is obeyed.

Those combinations of the two sunscreens which produce 'actual' transmission of the erythemally effective UV light (defined as 100/SPF) 1.1%, 1.3%, 1.5%, 1.7% and 1.8% higher than that of the single sunscreens are then plotted as in FIG. 1 to define the preferred, particularly preferred, especially preferred, more preferred and most preferred areas designated A, B, C, D, E on FIG. 1.

Evidence to confirm superiority of mixtures of ultrafine titanium dioxide (TiO$_2$) and octyl methoxycinnamate (Parsol MXC) whose respective weight concentrations both fall within the Area designated A in the accompanying drawing A sunscreen composition prepared as a conventional o/w emulsion containing either 9.15% ultrafine TiO$_2$ or 5.97% Parsol MCX gives a Sun Protective Factor (SPF) of 10.4 in the in vitro SPF method described hereinbefore. This indicates that the composition transmits 100/10.4 or 9.61% of incident erythemally effective UV light.

It would be expected that a similar composition containing $(9.15 \times 0.3)\%$ $TiO_2$ and $(5.97 \times 0.7)\%$ Parsol MCX would be equivalent to the formulation containing either sunscreen alone as above and in fact this is approximately the case as the SPF of the combination is 11.54 giving an erythemally effective UV light transmission of 8.66% just 0.95% less than predicted.

The composition containing $9.15 \times 0.3 = 2.74\%$ $TiO_2$ and $5.97 \times 0.7 = 4.2\%$ Parsol MCX lies outside the Area designated A on the accompanying figure, as it provides less than 1% unexpected additional absorbance of erythemally effective UV light.

A similar composition prepared containing either 12.6% $TiO_2$ or 15% Parsol MCX gives an SPF or 23.8 by the in vitro method, an erythemally effective UV light transmission of 4.2% (1/23.8). In this case however a composition containing $(0.7 \times 12.6)\%$ $TiO_2$ and $(0.3 \times 15\%)$ Parsol MCX gives an erythemally effective UV transmission of only 2.46%, an unexpected additional absoption of 1.74% of the erythemally effective UV light. This composition, which falls within the particularly preferred region of the figure, inside line D, containing $0.7 \times 12.6 = 8.82\%$ $TiO_2$ and $0.3 \times 15 = 4.5\%$ Parsol MCX gives a highly significant unexpected additional absorption.

EXAMPLES

The invention is illustrated by the following examples.

EXAMPLE 1

| Ingredient | % w/w |
| --- | --- |
| volatile siloxane (DC 345) | 8.20 |
| silicone surfactant (DC 3225C) | 12.00 |
| petroleum jelly | 0.50 |
| mineral oil | 1.50 |
| Parsol MCX (octyl methoxycinnamate) | 6.00 |
| ultrafine titanium dioxide (oil-dispersible) | 4.00 |
| sodium chloride | 2.00 |
| butylene glycol | 10.00 |
| l-proline | 0.10 |
| 2-hydroxy octanoic acid | 1.00 |
| 2-hydroxy propanoic acid | 5.00 |
| neutralising agent | qs |
| preservative | qs |
| perfume | qs |
| water | qs |

EXAMPLE 2

This example illustrates a cream according to the invention.

| Ingredient | % w/w |
| --- | --- |
| volatile siloxane (DC 345 Fluid) | 8.2 |
| silicone surfactant (DC 3225C) | 12.0 |
| mineral oil | 1.5 |
| petroleum jelly | 0.5 |
| Parsol MCX (octyl methoxycinnamate) | 10.0 |
| ultrafine titanium dioxide (oil-dispersible) | 8.0 |
| 2-hydroxyoctanoic acid | 1.0 |
| 2-hydroxypropanoic acid | 5.0 |
| sodium chloride | 2.0 |
| butylene glycol | 10.0 |
| l-proline | 0.10 |
| neutralising agent | q.s. |
| preservative | q.s. |
| perfume | q.s. |
| water | to 100 |

EXAMPLE 3

This example illustrates a lotion according to the invention.

| Ingredient | % w/w |
| --- | --- |
| silicone surfactant (DC 3225C) | 10.00 |
| volatile siloxane (DC 345) | 14.00 |
| mineral oil | 1.50 |
| Parsol MCX | 6.00 |
| Benzophenone-3 | 6.00 |
| Octyldimethyl PABA | 8.00 |
| Octyl salicylate | 6.00 |
| ultrafine titanium dioxide (oil-dispersible) | 8.00 |
| butylene glycol | 10.00 |
| sodium chloride | 2.00 |
| l-proline | 0.10 |
| 2-hydroxy octanoic acid | 1.00 |
| 2-hydroxy propanoic acid | 5.00 |
| neutralising agent | qs |
| perfume | qs |
| preservative | qs |
| water | qs |

EXAMPLE 4

This example illustrates a lotion according to the invention.

| Ingredient | % w/w |
| --- | --- |
| silicone surfactant | 10.00 |
| volatile siloxane | 14.00 |
| mineral oil | 1.50 |
| Parsol MCX | 5.00 |
| ultrafine titanium dioxide (water-dispersible) | 5.00 |
| ultrafine titanium dioxide (oil-dispersible) | 2.50 |
| 2-hydroxy octanoic acid | 1.00 |
| 2-hydroxy propanoic acid | 5.00 |
| butylene glycol | 10.00 |
| sodium chloride | 2.00 |
| amino acid | 0.10 |
| neutralising agent | qs |
| preservative | qs |
| perfume | qs |
| water | qs |

We claim:

1. A composition for topical application to human skin to provide protection from excessive exposure to ultra-violet rays, which comprises:
    (a) an effective amount of titanium dioxide having an average particle size of less than 100 nm as an inorganic sunscreen;
    (b) an effective amount of octyl methoxycinnamate as an organic sunscreen; and
    (c) a cosmetically acceptable vehicle for the sunscreens;
the weight concentration of the titanium dioxide and octyl methoxycinnamate being within the region designated D in the accompanying drawing.

2. The composition according to claim 1, wherein the titanium dioxide is water-dispersible titanium dioxide having a hydrophilic surface.

3. The composition according to claim 1, wherein the titanium dioxide is oil-dispersible titanium dioxide having a hydrophilic surface.

4. The composition according to claim 1, wherein the weight concentration of the titanium dioxide and octyl methoxycinnamate fall within the region designated E in the accompanying drawing.

5. The composition according to claim 1, which is an emulsion.

6. The composition according to claim 1, which comprises a silicone oil.

7. The composition according to claim 1, which comprises a silicone surfactant.

8. The composition according to claim 1, which further comprises a second organic sunscreen.

9. A method for protecting human skin from the harmful of excessive exposure to ultra-violet rays, which comprise the step of applying to the skin an effective amount of the composition according to claim 1.

* * * * *